United States Patent [19]
Rinehart et al.

[11] Patent Number: 5,478,932
[45] Date of Patent: Dec. 26, 1995

[54] ECTEINASCIDINS

[75] Inventors: Kenneth L. Rinehart, Urbana, Ill.; Ryuichi Sakai, Yokohama, Japan

[73] Assignee: The Board of Trustees of the University of Illinois, Urbana, Ill.

[21] Appl. No.: 161,340

[22] Filed: Dec. 2, 1993

[51] Int. Cl.$^6$ ............................................. C07D 515/22
[52] U.S. Cl. ............................................................. 540/466
[58] Field of Search .............................. 540/466; 544/339

[56] References Cited

U.S. PATENT DOCUMENTS

| | | | |
|---|---|---|---|
| 5,089,273 | 2/1992 | Rinehart et al. | 530/855 |
| 5,149,804 | 9/1992 | Rinehart et al. | 540/466 |
| 5,256,663 | 10/1993 | Rinehart et al. | 514/250 |

OTHER PUBLICATIONS

Guan et al Jour. Biomolec. Struc. & Dynam. vol. 10 pp. 793–817 (1993).
Sakai et al. Proc. Natl. Acad. Sci. USA vol. 89 pp. 11456–11460 (1992).
Guan et al, Chem. Abstr vol. 119 Entry 160608 (1993).
Sakai et al, Chem. Abstr vol. 118 Entry 160639 (1992).
Shamma et al., Carbon–13 NMR Shift Assignments of Amines and Alkaloids, p. 206 (1979).
Lown et al., Biochemistry, 21, 419–428 (1982).
Zmijewski et al., Chem. Biol. Interactions, 52, 361–375 (1985).
Ito, CRC Crit. Rev. Anal. Chem., 17, 65–143 (1986).
Rinehart et al., "Topics in Pharmaceutical Sciences 1989" pp. 613–626, D. D. Breimer, D. J. A. Cromwelin, K. K. Midha, Eds., Amsterdam Medical Press B.V., Noordwijk, The Netherlands (1989).
Rinehart et al., Biological Mass Spectrometry, 233–258 eds. Burlingame et al., Elsevier Amsterdam (1990).
Rinehart et al., Pure & Appl. Chem., vol. 62, No. 7, pp. 1277–1280 (1990).
Rinehart et al., Journal of Natural Products, vol. 53, No. 4, pp. 771–792 (1990).
Rinehart et al., J. Org. Chem., 55, 4512–4515 (1990).
Wright et al., J. Org. Chem., 55, 4508–4512 (1990).

*Primary Examiner*—Donald G. Daus
*Attorney, Agent, or Firm*—Ernest V. Linek

[57] ABSTRACT

Ecteinascidins (Et's), isolated from the Caribbean tunicate *Ecteinascidia turbinata*, protect mice in vivo against P388 lymphoma, B16 melanoma, M5076 ovarian sarcoma, Lewis lung carcinoma, and the LX-1 human lung and MX-1 human mammary carcinoma zenografts.

4 Claims, No Drawings

ECTEINASCIDINS

STATEMENT OF GOVERNMENTS SUPPORT

This work was supported in part by a grant from the National Institutes of Health (AI04769). Thus the Government of the United States of America has certain rights in this invention.

CROSS-REFERENCE TO RELATED APPLICATIONS

This application is related to U.S. Pat. Nos. 5,256,663, 5,149,804, and 5,089,273, the disclosures of which are hereby incorporated herein by reference.

BACKGROUND OF THE INVENTION

Several ecteinascidins (or Et's) have been reported previously in the patent and scientific literature. See, for example, Holt, T. G. Ph.D. Thesis, (University of Illinois, Urbana), (1986); Chem. Abstr., 106, 193149u; (1987); Diss. Abstr. Inc. B, 47, 3771–3772 (1987); Rinehart et al., U.S. patent application Ser. No. 872,189, filed Jun. 9, 1986; PCT Intl. Appln. WO87 07,610, filed Dec. 17, 1987; Chem. Abstr., 109, 811j. (1988); Rinehart et al., in Topics in Pharmaceutical Sciences 1989, eds. Breimer et al., (Amsterdam Medical Press B. V., Noordwijk, The Netherlands), pp. 613–626 (1989); Rinehart et al., in Biological Mass Spectrometry, pp. 233–258, eds. Burlingame et al., (Elsevier, Amsterdam (1990)), (1990); Rinehart et al., J. Nat. Prod., 53, 771–792, (1990); Rinehart et al., Pure Appl. Chem., 62, 1277–1280 (1990); Rinehart et al., J. Org. Chem., 55, 4512–4515, (1990); see also, Sakai et al., Proc. Natl. Acad. Sci., 89, 11456–460, dated Dec. 1, 1992.

Other ecteinascidins (Et's), e.g., Et's 729, Compound 1, 743, Compound 2, (see structure infra) and their derivatives, were isolated from the Caribbean tunicate *Ecteinascidia turbinata*, and two Et's (729 and 743) were later described by others. (See for example, Wright et al., J. Org. Chem., 55, 4508–4512 (1990)).

Et's 729 and 743, Compounds 1 and 2, are currently undergoing preclinical evaluation from the National Cancer Institute on the basis of exceedingly potent activity in vivo against a variety of tumor models in mice (cf. below). The major component, Et 743, Compound 2, and the others were assigned tris(tetrahydroisoquinoline) structures by correlation NMR techniques, as well as by FABMS and tandem MS (FABMS/MS).

However, the NMR data observed, including NOE's, did not allow unambiguous stereochemical assignment at C-1' in the C-subunit or at C-4 in the B-subunit and the minute quantities isolated limited further chemical investigation of these Compounds. Recently additional Et's, Compounds 5 through 7, as well as Compounds 1 and 2 have been isolated and characterized. Recrystallization of Compounds 5 and 4, a 21-O-methyl derivative of Compound 3, gave single crystals which allowed X-ray analyses of these remarkable compounds (see, Sakai, PNAS 1992, supra).

SUMMARY OF THE INVENTION

The present invention is directed, in part, to two new ecteinascidin (Et) compounds, namely 21-O-methyl-$N^{12}$-formyl Et 729 (Compound 4), derivatized from Compound 3, and the naturally occurring Et 743 $N^{12}$-oxide (Compound 5), structures for which were both determined by X-ray crystallography (PNAS, 1992, supra). These compounds (or their precursors) were isolated from *E. turbinata* samples collected in Puerto Rico.

Ecteinascidins (Et's), isolated from the Caribbean tunicate *Ecteinascidia turbinata*, protect mice in vivo against several tumors, including P-388 lymphoma, B-16 melanoma, M-5076 ovarian sarcoma, Lewis lung carcinoma, and the LX-1 human lung and MX-1 human mammary carcinoma xenografts. Crystal structures of two tris(tetrahydroisoquinoline) ecteinascidins were investigated using single crystals of the 21-O-methyl-$N^2$-formyl derivative of Et 729 (Compound 4) and the naturally occurring $N^{12}$-oxide of Et 743 (Compound 5).

The ecteinascidin (Et) compounds disclosed and/or claimed herein have the following structural formulas, and the numeric designations given for each after the abbreviation Et represent the masses (M) derived from the highest mass ions (M+H) observed in positive ion FABMS spectra.

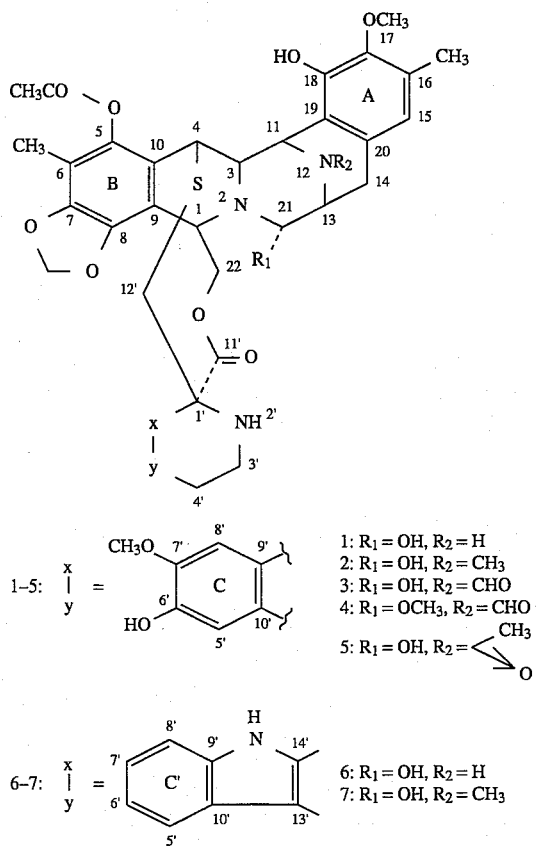

DETAILED DESCRIPTION OF THE INVENTION

Isolation of Ecteinascidins (Et's)

The cytotoxic extracts of *E. turbinata* were separated by using solvent partition, high speed countercurrent chromatography (HSCCC), and normal and reversed-phase chromatography. The compounds isolated were the previously known Et's 729 and 743 (Compounds 1 and 2), together with the $N^{12}$-oxide of 743 (Compound 5), and two additional Et's, 722 (Compound 6) and 736 (Compound 7). In addition, chromatography of Et 729 employing a formate buffer yielded its $N^{12}$-formyl derivative (Compound 3), which on crystallization from methanol gave that Compound's O-methyl analog (Compound 4).

Structures of Tetrahydro-β-carboline-containing Et's

Molecular formulas for Compound 6 ($C_{39}H_{40}N_4O_9S$) and Compound 7 ($C_{40}H_{42}N_4O_9S$) were assigned based on negative and positive ion HRFABMS data. $^1H$ and $^{13}C$ NMR spectra for Compound 6 vis-a-vis Compound 7 lacked the latter's $N^{12}$-$CH_3$ signals at 2.49 and 40.9 ppm, respectively, and showed an upfield shift for the adjacent carbons C-11 and C-13 from 54.5 and 52.6 ppm to 48.0 and 46.9 ppm. respectively, indicating that Compound 6 was the $N^{12}$-demethyl analog of Compound 7.

Comparison of NMR data, including COSY, phase-sensitive COSY, CSCM, COLOC, and HMBC sequences, for Compound 7 with those for Compound 2 (Table 1, and similar comparison of Compound 6 with 1) indicated that the same bis(tetrahydro-isoquinoline) units A and B are present in all, since C-1 through C-22 differed by an average of only 0.9 pmm. This was supported by HRFABMS and FABMS/MS, showing the expected fragment ions for the A-B bis(tetrahydroisoquinoline) unit at 523, 495, 477, 463, 218, and 204 (see, Rinehart et al., J. Org. Chem., 55, 4512–4515 (1990)). In addition, the tandem FAB mass spectra for Compounds 7 and 2 were essentially identical for the key fragment ion m/z 493.1980 ($C_{27}H_{29}N_2O_7$).

The molecular formula ($C_{13}H_{12}N_2OS$) of the subunit C' was given by subtraction of the formula for unit A-B, $C_{27}H_{30}N_2O_8$, from the formula for Compound 7, which was supported by sulfur-containing fragment ions at 243.0593 for $C_{13}H_{11}N_2OS$ and 216.0699 for $C_{12}H_{12}N_2S$, found in both FAB and tandem FAB mass spectra. The $^{13}C$ NMR signals for this subunit include one carbonyl and eight aromatic/olefinic carbons, leaving three rings for the structure.

An ortho-disubstituted benzene ring is assigned to unit C' from the four aromatic signals at δ7.33 d, 6.92 td, 7.02 td, and 7.29 d (J=8.0, 8.0, 0.6 Hz), and this is expanded into a 2,3-dialkyl-substituted indole by the near identity of the chemical shifts for C-5' through C-10', plus C-13' and C-14' (116.9 d, 117.7 d, 120.7 d, 111.7 d, 135.6 s, 126.6 s, 129.3 s, 109.5 s, respectively), with those for the corresponding carbons of 2-methyl-1,2,3,4-tetrahydro-β-carboline, (see, Shamma et al., Carbon-13 NMR Shift Assignments of Amines and Alkaloids, p. 206., (Plenum Press, New York, 1979)). The unit C' is characterized as containing Ar—$CH_2CH_2$—N< from $^1H$ and $^{13}C$ chemical shifts for C-4' and H-4'; C-3' and H-3' (20.9 t, 2.63 m, 2H; 39.6 t, 3.30, 2.90 dr), and located at C-14' by COLOC and HMBC, which correlate C-14' with H-3' and H-4', and by ROESY, which correlates H-4' and H-5'. The remaining carbons of Compound 7 (C-1', 61.9 ppm, quaternary; C-12', 38.9, methylene; C-11', 171.2, carbonyl), have chemical shifts close to those of C-1'; C-12' and C-11' in Compound 2, and they, with the sulfur atom, are assembled readily into the tetrahydro-β-carboline system shown for Compound 7. A long-range COLOC and HMBC correlation between C-11' and H-22, along with the IR ($CCl_4$) absorption at 1753 cm$^{-1}$, agreed with an ester linkage between C-11' (carbonyl) and C-22. HMBC correlation between H-12' and C-4 also confirmed a C-4-S-C-12' linkage.

The structures assigned Et's 722 (Compound 6) and Et 736 (Compound 7) are related biogenetically to those of the Et 729–743 series, but their tetrahydro-β-carboline unit presumably comes from tryptamine instead of dopamine and, indeed, the water-soluble portion of the same *E. turbinata* extract yielded tryptamine itself. The Et 722 and 736 structures strongly support our previously proposed, (see, Rinehart et al., J. Nat. Prod., 53, 771–792, (1990) and Rinehart et al., J. Org. Chem., 55, 4512–4515, (1990)) biogenetic pathway, involving nucleophilic addition of a mercaptan to a quinone methide.

Antitumor Activities of Et's

Et's 722 (Compound 6) and 736 (Compound 7) inhibit L1210 leukemia cells to the extent of 90% in plate assays at 2.5 and 5.0 μg/ml, respectively. More importantly, Compound 6 is highly active in vivo in mice, giving T/C>265 (2/6 survivors) at 25 μg/kg day vs. P-388 leukemia cells, T/C 200 at 50 μg/kg vs. an LX-1 human lung carcinoma xenograft, and slightly active vs. M-5076 ovarian sarcoma and an MX-1 human mammary carcinoma xenograft. It is especially promising that some in vivo selectivity is seen; Compound 6 is more effective than Compound 1 vs. P-388 (T/C 190 at 12.5 μg/kg day, 1/6 survivors, for Compound 1) but Compound 1 is more active against B-16 (T/C 253 at 12.5 μg/kg), Lewis lung (T/C 0.00 at 25 μg/kg), LX-1 (T/C 0.00 at 25 μg/kg), M-5076 (T/C 204, 5/10 survivors, at 12.5 μpg/kg) and MX-1 (T/C 0.05 at 37.5 μg/kg), all values for Et 729.

The ecteinascidins have been shown to bind strongly with DNA, but do not form permanent covalent adducts, perhaps mirroring earlier reversible reactions of saframycin A and naphthyridinomycin with DNA (Lown et al., Biochemistry, 21, 419–428 (1982) and Zmijewski et al., Chem. Biol. Interactions, 52, 361–375 (1985)).

TABLE 1

$^1H$ and $^{13}C$ NMR Data . . Et's 743 (2) and 736 (7) in $CD_3OD$—$CDCl_3$
Chemical shift, δ, ppm, and multiplicity (J, Hz)

| | 2[b] | | 7[c] | |
|---|---|---|---|---|
| | $^{13}C$ | $^1H$ | $^{13}C$ | $^1H$ |
| 1 | 56.3, d | 4.78, br s | 54.8, d | 4.71, br s |
| 3 | 58.8, d | 3.72[d] | 57.8, d | 3.76, br s |
| 4 | 42.7, d | 4.58, br s | 42.3, d | 4.58, br s |
| 5 | 142.2, s | | 140.8, s | |
| 6 | 113.9, s | | 112.6, s | |
| 7 | 146.5, s[e] | | 154.4, s | |
| 8 | 141.9, s | | 140.5, s | |
| 9 | 116.0, s | | 115.4, s | |
| 10 | 122.0, s | | 120.9, s | |
| 11 | 55.6, d | 4.40, br d (3.5) | 54.5, d | 4.73, br s |

TABLE 1-continued $^1$H and $^{13}$C NMR Data .. Et's 743 (2) and 736 (7) in CD$_3$OD—CDCl$_3$
Chemical shift, δ, ppm, and multiplicity (J, Hz)

| | 2$^b$ | | 7$^c$ | |
|---|---|---|---|---|
| | $^{13}$C | $^1$H | $^{13}$C | $^1$H |
| 13 | 54.0, d | 3.52, br s | 52.6, d | 3.90, br s |
| 14 | 24.5, t | 2.91, 2 H, br d (4.5) | 23.2, t | 3.30$^f$ |
| | | | | 3.08, dd (10.0, 19.0) |
| 15 | 120.9, d | 6.55, s | 120.3, d | 6.70, s |
| 16 | 131.2, s | | 130.3, s | |
| 17 | 145.1, s | | 143.0, s | |
| 18 | 149.8, s | | 148.2, s | |
| 19 | 119.2, s | | 118.5, s | |
| 20 | 131.5, s | | 130.9, s | |
| 21 | 92.1, d | 4.26, d (3.0) | 91.5, d | 4.46, d (2.4) |
| 22 | 61.2, t | 5.14, d (11.0) | 62.0, t | 5.20, dd (12.5, 0.5) |
| | | 4.09, dd (11.0, 2.0) | | 4.18, dd (12.5, 1.5) |
| OCH$_2$O | 103.1, t | 6.07, d (1.0) | 101.7, t | 6.26, d (1.0) |
| | | 5.98, d (1.0) | | 6.07, d (1.0) |
| 1' | 65.3, s | | 61.9, s | |
| 3' | 40.3, t | 3.13, dt (4.0, 11.0) | 39.6, t | 3.30$^f$ |
| | | 2.77, ddd (3.5, 5.5, 11.0) | | 2.90 dt (11.5, 4.5) |
| 4' | 28.6, t | 2.60, ddd (5.5, 10.5, 16.0) | 20.9, t | 2.63, 2 H, m |
| | | 2.42, ddd (3.5, 3.5, 16.0) | | |
| 5' | 115.6, d | 6.38, s | 116.9, d | 7.33, d (8.0) |
| 6' | 146.4, s$^e$ | | 117.7, d | 6.92, td (8.0, 8.0, 0.6) |
| 7' | 146.4, s$^e$ | | 120.7, d | 7.02, td (0.68.0, 8.0, 0.6) |
| 8' | 111.3, d | 6.42, br s | 111.7, d | 7.29, d (8.0) |
| 9' | 125.4, s | | 135.6, s | |
| 10' | 128.8, s | | 126.6, s | |
| 11' | 173.1, s | | 171.2, s | |
| 12' | 43.1, t | 2.38, br d (15.5) | 38.9, t | 2.78, d (15.6) |
| | | 2.05$^d$ | | 2.15, br d (15.3) |
| 13' | | | 129.3, s | |
| 14' | | | 109.5, s | |
| 5 OAc(C=O) | 169.8, s | | 169.5, s | |
| 5 OAc(CH$_3$) | 20.5, q | 2.29, s | 20.3, q | 2.28, s |
| 6 CH$_3$ | 9.9, q | 2.01, s | 9.4, q | 2.02, s |
| 16 CH$_3$ | 16.1, q | 2.28, s | 15.7, q | 2.37, s |
| 17 OCH$_3$ | 60.2, q | 3.72, s | 60.0, q | 3.76, s |
| 7' OCH$_3$ | 55.7, q | 3.58, s | | |
| 12 NCH$_3$ | 41.1, q | 2.23, s | 40.9, q | 2.49, br s |

$^a$Proton assignments are made based on COSY and homonuclear decoupling experiments: carbon multiplicities were determined by APT and DEPT spectra. $^b$3:1 CD$_3$OD—CDCl$_3$. $^c$7:1 CD$_3$OD—CDCl$_3$. $^d$Signals overlap with methyl singlet. $^e$Assignments are interchangeable. $^f$Signals overlap with solvent peak.

EXAMPLES

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLE 1

Isolation and Purification of Et's 736, 722, 743-N$^{12}$ Oxide

A wet sample of tunicate collected in Puerto Rico in 1991 was extracted with isopropyl alcohol. The alcoholic extract was concentrated to leave an aqueous emulsion, which was extracted with ethyl acetate. The organic layer was concentrated, then partitioned with ethyl acetate-heptane-methanol-water (7:4:4:3). The lower layer was concentrated and the resulting solid was chromatographed on a C-18 gravity column, then by high speed counter current chromatography (HSCCC) (see for example, Ito, Y., CRC Crit. Rev. Anal. Chem., 17, 65, 143, (1986)). Each of the resulting fractions was monitored by FABMS and the fractions containing ecteinascidins were further separated by repeating reversed-phase HPLC (ODS) systems to afford pure Compounds 1, 2, 3, 5, 6 and 7, some of which showed the following physical properties:

Et 736 (Compound 7): fine needles (from CH$_3$CN—H$_2$O), mp 140°–150° C. dec.; [α]D-76° (c 0.53, CHCl$_3$); IR (CCl$_4$) 3530, 3480 (NH, OH), 2934, 1768 (ester), 1753 (ester), 1196, 1153, 1089 cm$^{-1}$, NMR, see Table I.

Anal. Calcd. for C$_{40}$H$_{41}$N$_4$O$_9$S (M-H): 753.2594. Found 753.2588 (negative ion FABMS).

Et 722 (Compound 6): yellowish amorphous solid, mp 160°–164° C.; [α]D-40° (c 1.64, CHCl$_3$); IR (film) 3292 (NH, OH), 2930, 1753 (C=O), 1440, 1238, 1200, 1086 cm$^{-1}$.

Anal. Calcd. for C$_{39}$H$_{39}$N$_4$O$_9$S (M-H): 739.2432. Found: 739.2433 (negative ion FABMS).

Et 743 N$^{12}$-Oxide (Compound 5): Colorless prisms (from CH$_3$CN), mp=150° C. dec.; [α]$^{25}$D—55° (c 0.22, CHCl$_3$); $^1$H NMR (500 MHz, CD$_3$OD) δ6.63 (s, 1H), 6.46 (br s, 1H), 6.39 (s, 1H), 6.12 (s, 1H), 6.03 and 6.02* (s, 1H), 5.17 and 5.15* (d, 1H, J=11.5 Hz), 5.07 (s, 1H, 4.85 (d, 1H, J=2 Hz) 4.78 (m, 1H), 4.65 (s, 1H), 4.48 and 4.35* (d, 1H, J=4 Hz), 4.16 (m, 1H), 3.98 and 4.02* (d, 1H, J=11.5 Hz), 3.74 (s, 3H), 3.59 (s, 3H), 3.05 and 3.00* (s, 3H), 2.32 (s, 3H), 2.30 (s, 3H), 2.04 (s, 3H).

*Peaks appeared as pairs (about 2:1 ratio).

Anal. Calcd. for $C_{39}H_{42}N_3O_{11}S$ (M+H–H$_2$O): 760.2546. Found: 760.2540 (negative ion FABMS).

EXAMPLE 2

$N^{12}$-Formyl Et 729 (Compound 3)

Compound 1 (27 mg) was passed through a semi-preparative HPLC column (IDS, 10×25 cm) with methanol-water (0.02M ammonium formate). The resulting broad peak ($t_r$ 38 min.) was collected and concentrated to give a solid (20 mg). HPLC (ODS) separation of the solid with methanol-water (9:2, 0.05M NaCl) recovered intact Compound 1 (5.4 mg) and Compound 3.

Anal. Calcd. for $C_{39}H_{40}N_3O_{12}S$ (M-H): 774.2333. Found 774.2337 (negative ion FABMS).

EXAMPLE 3

21-O-Methyl-$N^{12}$-formyl Et 729 (Compound 4)

Recrystallization of Compound 3 from methanol-water (10:1) gave Compound 4 (12.7 mg): yellowish crystals; mp=175° C. dec. $[\alpha]^{23}D$—79° (c 0.82, CHCl$_3$); $^1$H NMR (500 MHz, CDCl$_3$) δ8.18 and 7.85* (s, 1H), 6.56 and 6.55* (s, 1H), 6.41 (s), 6.36 and 6.33* (s, 1H), 6.01 (s), 5.93, 5.75 (d, 1H, J=5 Hz), 5.09 and 5.07* (d, 1H, J=10 Hz), 5.02 (m, 1H), 4.73 and 4.65* (s, 1H), 4.57 (br s, 1H), 4.09 (m, 2H), 3.80 (s, 3H), 3.70 and 3.69* (s, 3H), 3.56 and 3.55* (s, 3H), 3.20–3.00 (m, 3H), 2.84 (br m, 1H), 2.66 (br m, 1H), 2.55–2.35 (br m, 2H), 2.25 and 2.24* (s, 6H), 1.97 and 1.97* (s, 3H).

*Peaks appeared as pairs (about 2:3 ratio).

Anal. Calcd. for $C_{40}H_{42}N_3O_{12}S$ (M-H): 788.2489. Found: 788.2480 (negative ion FABMS).

EXAMPLE 4

Isolation and Purification of Et's 770 (Compound 8) and 756 (Compound 9)

A sample of *E. turbinata* (14.1 kg) collected at Gallows Point Reef in Belize was thawed and the water drained off through cheese cloth. The solids (2.0 kg) were divided into two portions of which one (371 g) was used for this experiment. This sample was homogenized in methanol (2×500 mL, 4×400 mL) and the extracts were filtered through a pad of celite. The first four extracts (1.7 L) were combined and potassium cyanide (340 mg) was added. The last two extracts (0.7 L) were also combined and treated with potassium cyanide (165 mg). These extracts were allowed to stand at –10° C. for 2.5 days. Silica TLC bioautography (3:1 ethyl acetate/methanol) of these crude methanol extracts against *M. luteus* showed that the main bioactive spot changed from $R_f$ 0.45 to $R_f$ 0.85 upon treatment with potassium cyanide.

Each of these combined extracts was partitioned by the addition of 1M sodium chloride (500 mL and 200 mL, respectively) and toluene (350 mL and 150 mL, respectively). The aqueous layer from each was then extracted with dichloromethane (3×350 mL and 2×150 mL, respectively). All of these dichloromethane extracts were combined and the solvent was removed to give a residue (433 mg) which was dissolved in methanol (250 mL) and extracted with hexane (4×250 mL). The methanol extract was concentrated and triturated with acetone, dichloromethane and methanol. The combined organic extracts (263.9 mg) were subjected to HSCC using the solvent system carbon tetrachloride/chloroform/methanol/water (7:3:8:2) with the lower phase as the mobile phase. This resulted in a series of nine fractions of which the fourth through the seventh and the ninth fractions contained the majority of the bioactivity.

These bioactive fractions (45 mg) were combined and further separated by MPLC on a CHP-20 porous column. A step gradient of methanol/0.05M Tris (buffered to pH 7 with hydrochloric acid) was used (85:15, 90:10, 95:5, 100:0). This produced a series of 11 fractions of which the fourth to the sixth exhibited the most bioactivity. Some of the Tris buffer was removed by extraction of each fraction with dichloromethane. These three bioactive fractions were each purified by C-18 HPLC using 75:25 methanol/0.05M Tris (buffered to pH 7 with hydrochloric acid). An attempt was made to remove the Tris buffer by partitioning between dichloromethane and water, but some buffer remained in the fractions. Ecteinascidin 756 (Compound 9) was obtained from the fourth MPLC fraction (0.27 mg, $7×10^{-5}$% yield), while the fifth and sixth MPLC fractions contained ecteinascidin 770 (Compound 8, 2.1 mg, $5.6×10^{-4}$% yield). The latter was confirmed to be the same compound isolated by Holt by comparison of the HPLC of this fraction with an authentic sample.

Ecteinascidin 756 (Compound 9): $t_r$ 8.7 min. [75:25 methanol/0.05M Tris (buffered to pH 7 with hydrochloric acid), 2.5 mL/min]; $R_f$ 0.19 (silica TLC, 9:1 chloroform/methanol).

Anal. Calcd. for $C_{39}H_{41}N_4O_{10}S$; 757.2543 (M+H). Found: 757.2539 (HRFABMS).

Ecteinascidin 770 (Compound 8): $t_r$ 14.3 min [75:25 methanol/0.05M Tris (buffered to pH 7 with hydrochloric acid), 2.5 mL/min]; $R_f$ 0.51 (silica TLC, 9:1 chloroform/methanol), 0.70 (silica TLC, 5:1 ethyl acetate/methanol).

Anal. Calcd. for $C_{40}H_{43}N_4O_{10}S$: 771.2700 (M+H). Found: 771.2704 (HRFABMS).

EXAMPLE 5

IN VITRO ACTIVITY OF COMPOUNDS 8 AND 9

Compounds 3 and 5 described herein were tested in vitro against the following cell lines; P-388 murine leukemia cell line; HT-29 human colon cancer cell line; A-549 human lung adenocarcinoma cell line; and CV-1 monkey kidney cell line (non-cancerous); and the IC$_{50}$ in μg/ml was determined. The results are reported below in Table II.

TABLE 11

| Et Compound | IC$_{50}$ in μg/ml against | | | |
|---|---|---|---|---|
| | P-388 | A-549 | HT-29 | CV-1 |
| Compound 3 | 0.0005 | 0.002 | 0.002 | 0.005 |
| 745B | 0.005 | 0.01 | 0.01 | 0.025 |
| Compound 5 | 0.001 | 0.0025 | 0.0025 | 0.0025 |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The $N^{12}$-oxide of ecteinascidin 743, substantially free of any cellular debris of *Ecteinascidia turbinata*, which has the following structure:

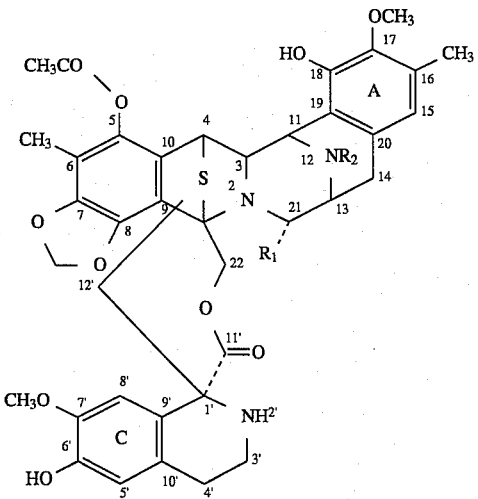

wherein $R_1$ is OH and $R_2$ is $OCH_3$.

2. The 21-O-methyl-$N^{12}$-formyl derivative of ecteinascidin 729, substantially free of any cellular debris of *Ecteinascidia turbinata*, which has the following structure:

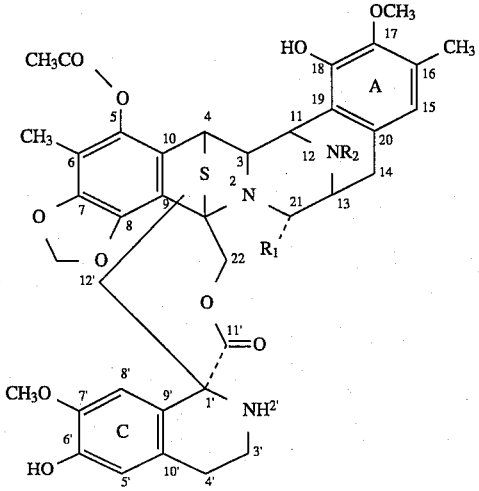

wherein $R_1$ is $OCH_3$ and $R_2$ is CHO.

3. The $N^{12}$-formyl derivative of ecteinascidin 729, which has the following structure:

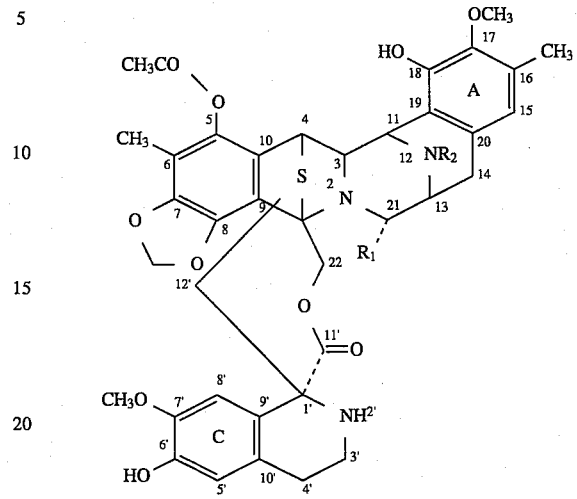

wherein $R_1$ is OH and $R_2$ is CHO.

4. The 21-cyano analog of ecteinascidin 729, which has the following structure:

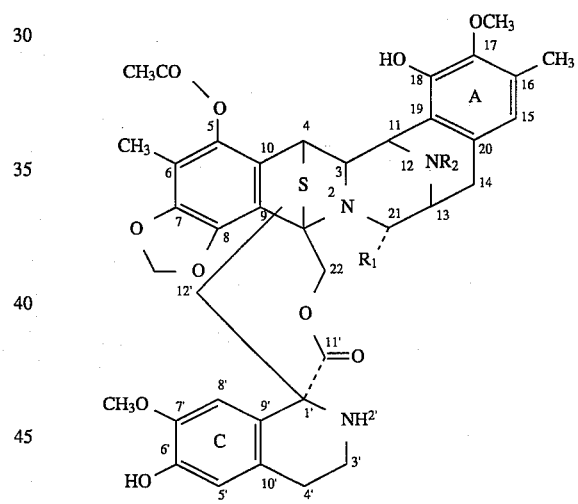

wherein $R_1$ is cyano and $R_2$ is H.

* * * * *

UNITED STATES PATENT AND TRADEMARK OFFICE
CERTIFICATE OF CORRECTION

PATENT NO. : 5,478,932
DATED : December 26, 1995
INVENTOR(S) : Kenneth L. Rinehart and Ryuichi Sakai It is certified that error appears in the above-indentified patent and that said Letters Patent is hereby corrected as shown below:

On the cover page, in the Abstract, item [57], line5, delete "zenografts" and insert --xenografts--.

At Column 8, line 43 (Title of Example 5), please change "COMPOUNDS 8 AND 9" to --COMPOUNDS 3 AND 5--.

Signed and Sealed this

Eleventh Day of February, 1997

Attest:

BRUCE LEHMAN

Attesting Officer    Commissioner of Patents and Trademarks